(12) United States Patent
Imura et al.

(10) Patent No.: US 7,198,810 B2
(45) Date of Patent: Apr. 3, 2007

(54) YEAST

(75) Inventors: Toshiaki Imura, Tsukuba (JP); Hideki Kawasaki, Machida (JP)

(73) Assignee: Kyowa Hakko Food Specialties Co., Ltd., Tokyo (JP)

( * ) Notice: Subject to any disclaimer, the term of this patent is extended or adjusted under 35 U.S.C. 154(b) by 56 days.

(21) Appl. No.: 10/369,715

(22) Filed: Feb. 21, 2003

(65) Prior Publication Data

US 2003/0161911 A1 Aug. 28, 2003

(30) Foreign Application Priority Data

Feb. 21, 2002 (JP) .............................. 2002/044331
May 28, 2002 (JP) .............................. 2002/153853

(51) Int. Cl.
*A21D 2/08* (2006.01)
*C12N 1/18* (2006.01)

(52) U.S. Cl. ........................ 426/27; 426/549; 426/561; 435/255.2

(58) Field of Classification Search ................ 426/19, 426/27, 62, 549, 561, 656; 435/255.2
See application file for complete search history.

(56) References Cited

U.S. PATENT DOCUMENTS 5,997,914 A * 12/1999 Shimura et al. .............. 426/27
6,649,198 B2 * 11/2003 Imura et al. .................. 426/19
6,660,311 B2 * 12/2003 Goedeken et al. ............ 426/27

FOREIGN PATENT DOCUMENTS

EP 0 588 426 3/1994
JP 10-191964 7/1998

OTHER PUBLICATIONS

Y. Kyogoku, et al., "Isolation of a Cold-Sensitive Fermentation Mutant of a Baker's Yeast Strain and Its Use in a Refrigerated Dough Process", Applied and Environmental Microbiology, vol. 61, No. 2, Feb. 1995, pp. 639-642.
A. Rincón, et al., "Improved Properties of Baker's Yeast Mutants Resistant to 2-Deoxy-D-Glucose", Applied and Environmental Microbiology, vol. 67, No. 9, Sep. 2001, pp. 4279-4285.

* cited by examiner

*Primary Examiner*—Keith Hendricks
(74) *Attorney, Agent, or Firm*—Antonelli, Terry, Stout & Kraus, LLP.

(57) ABSTRACT

The present invention provides yeast belonging to the genus *Saccharomyces* which generates, in dough containing 5% sugar, carbon dioxide gas in an amount of not less than 2.0 ml per g of the dough and not less than 1.20 ml per ml of volume expansion of the dough at 38° C. in 60 minutes; a method of screening for the yeast; bread dough containing the yeast; a process for making bread using the yeast; and bread having an anti-mold effect which is obtained by the process.

21 Claims, 2 Drawing Sheets

YEAST

BACKGROUND OF THE INVENTION

The present invention relates to yeast, a method of screening for yeast, bread dough, a process for making bread, and bread.

As the commercial value of bread is materially reduced by the growth of molds, anti-mold measures such as promotion of the environmental cleanliness and addition of various anti-mold agents are generally taken in the production of bread.

The anti-mold agents generally employed include those containing an acidulant such as acetic acid, an additive such as sodium acetate and a bactericide such as propionic acid or ethanol. However, the addition of such anti-mold agents has the undesirable effect of deteriorating the flavor of bread. Also in view of a growing nature-oriented trend in recent years, there exists a strong demand for the establishment of technology to inhibit the growth of molds without addition of anti-mold agents.

However, it is difficult to inhibit the growth of molds without adding an anti-mold agent in conventional bread-making processes.

An object of the present invention is to provide yeast used for making bread having an anti-mold effect, a method of screening for the yeast, bread dough containing the yeast, a process for making bread which comprises adding the yeast to bread dough, and bread obtained by the process.

SUMMARY OF THE INVENTION

The present invention relates to the following (1) to (14).
(1) Yeast belonging to the genus *Saccharomyces*, which generates, in dough containing 5% sugar, carbon dioxide gas in an amount of not less than 2.0 ml per g of the dough and not less than 1.20 ml per ml of volume expansion of the dough at 38° C. in 60 minutes. In the present specification, "dough containing 5% sugar" means dough which contains 5 parts by weight of sugar per 100 parts by weight of flour.
(2) The yeast according to the above (1), wherein the yeast belongs to *Saccharomyces cerevisiae*.
(3) The yeast according to the above (1) or (2), wherein the yeast is *Saccharomyces cerevisiae* YHK1923 (FERM BP-7901) or *Saccharomyces cerevisiae* YHK2931 (FERM BP-8046).
(4) Bread dough containing the yeast according to any of the above (1) to (3).
(5) A process for making bread which comprises using the yeast according to any of the above (1) to (3).
(6) A process for making bread which comprises using the bread dough according to the above (4).
(7) Bread obtained by the process according to the above (5) or (6).
(8) A method of screening for yeast which comprises selecting yeast which generates, in dough containing 5% sugar, carbon dioxide gas in an amount of not less than 2.0 ml per g of the dough and not less than 1.20 ml per ml of volume expansion of the dough at 38° C. in 60 minutes.
(9) Yeast obtained by the method according to the above (8).
(10) Bread dough containing the yeast according to the above (9).
(11) A process for making bread which comprises using the yeast according to the above (9).
(12) A process for making bread which comprises using the bread dough according to the above (10).
(13) Bread obtained by the process according to the above (11) or (12).
(14) The bread according to the above (7) or (13), which has a high ethanol content.

DETAILED DESCRIPTION OF THE INVENTION

Figure 1:
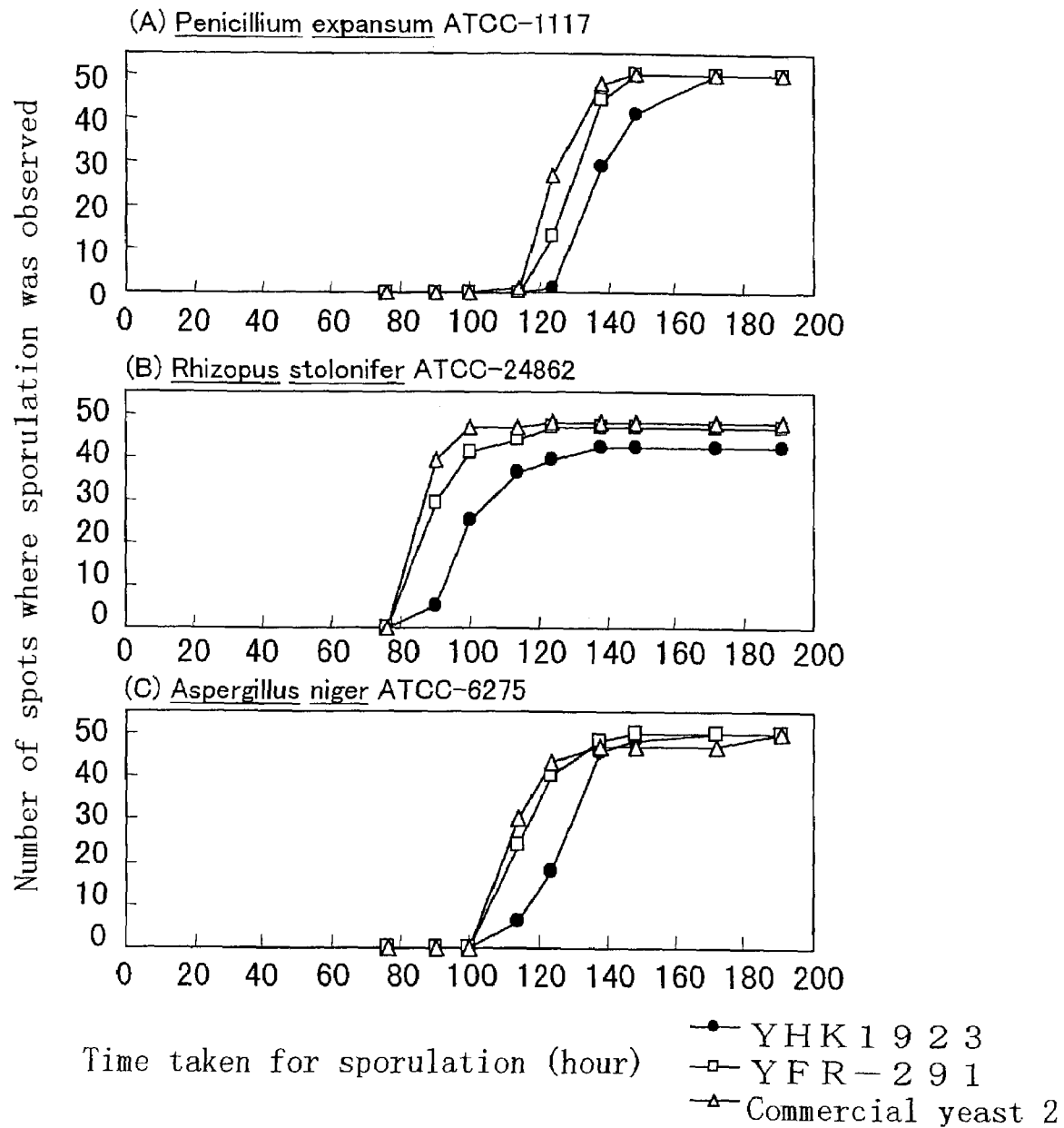
FIG. 1 shows the results of measurement of the time taken for mold to sporulate on three loaves of bread made using YHK1923 strain, YFR-291 strain and commercial yeast 2, respectively. The numbers on the abscissa of each graph indicate the time lapse after the inoculation of mold spores onto bread and those on the ordinate indicate the number of spots where sporulation was observed. The graphs respectively show the results of the measurement of the time taken for mold to sporulate with respect to (A) *Penicillium expansum* ATCC-1117, (B) *Rhizopus stolonifer* ATCC-24862 and (C) *Aspergillus niger* ATCC-6275. The symbols refer to the strains used for production of bread as follows: ● YHK1923 strain, □ YFR-291 strain, and Δ commercial yeast 2.

The yeast of the present invention includes those which generate, in dough containing 5% sugar, carbon dioxide gas in an amount of not less than 2.0 ml, preferably not less than 2.4 ml, more preferably not less than 3.0 ml per g of the dough and not less than 1.20 ml, preferably not less than 1.40 ml per ml of volume expansion of the dough at 38° C. in 60 minutes, when the volume expansion of the dough is measured by 7 sequent steps of the following (i) to (vii) and the amount of generated carbon dioxide gas is measured by 7 sequent steps of the following (i) to (iv) and (viii) to (x) using the yeast cells obtained according to the following steps (a) to (d):
(a) a step in which one loopful of yeast cells is inoculated on YM medium (1 l of water, 10 g of glucose, 5 g of peptone, 3 g of yeast extract, 3 g of malt extract and 20 g of agar, pH 6) previously sterilized at 120° C. for 20 minutes, followed by culturing at 30° C. for 2 days;
(b) a step in which one loopful of the yeast cells obtained in step (a) is inoculated into YPD medium (30 ml of water, 0.3 g of yeast extract, 0.6 g of polypeptone and 0.6 g of glucose) in a 300-ml Erlenmeyer flask previously sterilized at 120° C. for 20 minutes, followed by shaking culture (220 rpm) at 30° C. for 24 hours;
(c) a step in which the whole of the culture obtained in step (b) is inoculated into a molasses medium (300 ml of water, molasses in the amount corresponding to 3% (w/v) sugar, 0.579 g of urea, 0.138 g of potassium dihydrogenphosphate and 2 drops of defoaming agent) in a 2-l Erlenmeyer flask with an inclined baffle previously sterilized at 120° C. for 20 minutes, followed by shaking culture (220 rpm) at 30° C. for 24 hours;

(d) a step in which the cells are separated from the culture obtained in step (c) by centrifugation (3,000 rpm, 5 minutes, 4° C.) and are washed three times with deionized water, followed by suction filtration using a Nutsche funnel to obtain the yeast cells;

(i) a step in which 100 g of strong flour, a yeast suspension comprising 2 g of the yeast cells obtained by steps (a) to (d) and 20 ml of water, and an aqueous solution comprising 5 g of sugar, 2 g of salt and 42 ml of water are mixed and kneaded using National Complete Mixer at 100 rpm for two minutes so that the temperature of the resultant dough becomes 28 to 30° C.;

(ii) a step in which the dough obtained in step (i) is rounded and packed into a 600-ml glass cylinder [diameter (inner diameter): 5.7 cm, height: 24 cm, thickness: 0.5 cm, with both ends open] which has been previously warmed at 30° C. and whose inside is coated with lubricant oil, from the bottom with the smooth side up;

(iii) a step in which the cylinder of step (ii) is put on a dish previously warmed at 30° C., and after the surface of the dough is flattened with a rolling pin, the upper end of the cylinder is covered with a wet cloth, followed by incubation at 30° C. at 85% relative humidity for 2.5 hours;

(iv) a step in which the dough obtained in step (iii) is taken out and subjected to punching, and two pieces (100 g and 20 g) are divided from the dough;

(v) a step in which 100 g piece of the dough obtained in step (iv) is rounded and packed into the glass cylinder described in step (ii) from the bottom with the smooth side up;

(vi) a step in which the cylinder of step (v) is put on the dish described in step (iii); after the surface of the dough is flattened with a rolling pin, the height of the top of the dough is measured and the upper end of the cylinder is covered with a wet cloth, followed by incubation at 38° C. at 85% relative humidity for 60 minutes; and the height of the top of the dough is measured again;

(vii) a step in which the volume expansion of the dough is calculated from the difference between the height of the top of the dough before incubation and that after incubation measured in step (vi);

(viii) a step in which 20 g piece of the dough obtained in step (iv) is put in a 225-ml sample bottle and the bottle is capped with a cap which has a tube connected to a fermograph, for example, Fermograph II (ATTO Corporation);

(ix) a step in which the sample bottle of step (viii) is kept at 38° C. for 5 minutes;

(x) a step in which the amount of carbon dioxide gas generated from the dough when the sample bottle of step (ix) is kept at 38° C. for 60 minutes is measured using the fermograph.

In step (d), the ratio of the weight of dry yeast cells (hereinafter referred to as the dry weight) to the weight of yeast cells is adjusted to 25 to 40% (w/w). The ratio of the dry weight to the weight of yeast cells can be calculated in the following manner.

Yeast cells (ca. 3 g) (A) is weighed and dried at 105° C. for 5 hours. The dry weight of the obtained yeast cells is measured and regarded as B. The ratio of the dry weight (%) is calculated by the following equation.

Ratio of the dry weight of yeast cells (%)=100×(B/A)

The amount of the yeast cells used in the above step (i) (2 g) is that when the ratio of the dry weight is 33% (w/w). When the ratio of the dry weight is not 33% (w/w), the amount calculated by the following equation is employed in place of the amount of yeast cells to be used when the ratio of the dry weight is 33% (w/w) (2 g).

Amount of yeast cells to be used in step (i) (g)=2×33/ratio of the dry weight to the weight of yeast cells The volume expansion of dough per g of dough can be calculated from the volume expansion of dough measured by 7 sequent steps of the above steps (i) to (vii).

The amount of carbon dioxide gas generated per g of dough can be calculated from the amount of generated carbon dioxide gas measured by 7 sequent steps of the above steps (i) to (iv) and (viii) to (x).

The amount of carbon dioxide gas generated per ml of volume expansion of dough can be calculated from the amount of carbon dioxide gas generated per g of dough and the volume expansion per g of dough.

The yeast of the present invention can be obtained, for example, by screening yeasts isolated from nature, preferably those belonging to the genus *Saccharomyces*, more preferably those belonging to *Saccharomyces cerevisiae*, for strains having the above characteristics.

The yeast of the present invention can also be obtained by subjecting yeasts such as baker's yeast, sake yeast, wine yeast, beer yeast and miso and soy sauce yeast, preferably those belonging to the genus *Saccharomyces* to known mutagenesis such as ultraviolet irradiation, X-radiation, treatment with mutagens such as ethyl methanesulfonate and N-methyl-N'-nitro-N-nitrosoguanidine, gene manipulation and hybridization breeding, and then screening the obtained mutants for strains having the above characteristics.

Specific examples of the yeast of the present invention are *Saccharomyces cerevisiae* YHK1923 (FERM BP-7901, hereinafter referred to as YHK1923 strain), *Saccharomyces cerevisiae* YHK2766 (hereinafter referred to as YHK2766 strain) and *Saccharomyces cerevisiae* YHK2931 (FERM BP-8046, hereinafter referred to as YHK2931 strain).

The yeast of the present invention can be cultured under ordinary culturing conditions for yeast, for example, in a medium containing carbon sources, nitrogen sources, inorganic substances, amino acids, vitamins, etc. under aerobic conditions at 27 to 32° C.

Examples of the carbon sources are glucose, sucrose, starch hydrolyzate and molasses, and preferred is molasses.

Examples of the nitrogen sources are ammonia, ammonium chloride, ammonium sulfate, ammonium carbonate, ammonium acetate, ammonium phosphate, urea, yeast extract and corn steep liquor.

Examples of the inorganic substances are magnesium phosphate and potassium phosphate. An example of the amino acids is glutamic acid, and examples of the vitamins are pantothenic acid and thiamine. Culturing is preferably carried out by fed batch culture.

After the completion of the culturing, yeast cells are separated from the culture and washed by an ordinary method, and then suspended in water to prepare a yeast suspension useful for the production of bread dough and bread. The cells may be recovered from the obtained yeast suspension and dehydrated using a filter such as a rotary vacuum dehydrator or a filter press to prepare compressed yeast cells having the water content of 60 to 75% (w/w) (hereinafter referred to as compressed yeast), or the compressed yeast may further be dried with a dryer to prepare dried yeast cells having the water content of 2 to 12% (w/w). These compressed yeast and dried yeast cells can also be used for the production of bread dough and bread.

The bread dough of the present invention can be obtained by adding to grain flour, usually wheat flour, the yeast of the present invention, salt and water, and if necessary sugar, skim milk, eggs, yeast food, shortening, butter, etc., followed by mixing and kneading.

Production of bread according to the present invention can be carried out by ordinary breadmaking methods using the yeast of the present invention.

There are two kinds of typical methods for making one-loaf bread, buns, etc.; that is, the straight dough method and the sponge and dough method. The former is a method in which all the ingredients of dough are mixed at a time. The latter is a method in which at first a sponge is made by kneading a part of grain flour with yeast and water, and then, after fermentation, the remaining ingredients are added to the sponge.

In the straight dough method, all the ingredients of dough are mixed and kneaded, and the kneaded mixture is fermented at 25 to 30° C. The fermented dough is subjected to the following steps: dividing, benching, molding, proofing (35 to 42° C.) and baking (200 to 240° C.).

In the sponge and dough method, about 70% of the grain flour to be used, yeast and yeast food are mixed and kneaded with water. The kneaded mixture is fermented at 25 to 35° C. for 2 to 5 hours, and then mixed and kneaded with the remaining ingredients such as grain flour, water, salt, sugar, skim milk and shortening (dough mixing). The obtained dough is subjected to the following steps: floor time, dividing, benching, molding, proofing (35 to 42° C.) and baking (200 to 240° C.).

Bread having a high ethanol content can be obtained by the above methods. As used herein, the term "having a high ethanol content" means "containing ethanol at a concentration high enough to exert a sufficient anti-mold effect". The ethanol concentration is preferably 0.8% (w/w) or higher, more preferably 0.9% (w/w) or higher, further preferably 1.0% (w/w) or higher in the case of one-loaf bread. It is also preferable that the ethanol concentration is below 1.5% (w/w) to avoid deterioration of flavor.

Certain embodiments of the present invention are illustrated in the following examples.

EXAMPLE 1

One loopful of *Saccharomyces cerevisiae* YFR-291 was inoculated into 50 ml of YPD medium (1% (w/v) yeast extract, 2% (w/v) polypeptone and 2% (w/v) glucose), followed by shaking culture at 30° C. for 16 hours. The resulting culture was centrifuged to collect cells, and the collected cells were washed twice with sterile water and suspended in 27.6 ml of a 0.2 mol/l phosphate buffer. To the resulting suspension were added 1.5 ml of a 40% (w/v) glucose solution and 0.9 ml of ethyl methanesulfonate, followed by gentle shaking at 30° C. for 180 minutes. Then, the cells were collected from the cell suspension and neutralized with a 5% (w/v) solution of sodium thiosulfate for 10 minutes. After being washed three times with sterile water, the cells were suspended in 10 ml of sterile water. The resulting cell suspension was spread on YPD plate medium and cultured at 30° C. for 48 hours to grow colonies. Yeast cells were obtained from one of the colonies according to the above steps (a) to (d). The volume expansion of the dough prepared using the obtained yeast cells was measured according to 7 sequent steps of the above steps (i) to (vii), and the amount of generated carbon dioxide gas was measured according to 7 sequent steps of the above steps (i) to (iv) and (viii) to (x). As a result, a strain was obtained which generated, in dough containing 5% sugar, carbon dioxide gas in an amount of not less than 2.0 ml per g of the dough and not less than 1.20 ml per ml of volume expansion of the dough at 38° C. in 60 minutes. The obtained strain was named YHK1923 strain and was deposited with International Patent Organism Depositary, National Institute of Advanced Industrial Science and Technology, Central 6, 1—1, Higashi 1-chome, Tsukuba-shi, Ibaraki 305-8566, Japan, on Feb. 18, 2002 under the Budapest Treaty with accession No. FERM BP-7901.

EXAMPLE 2

One loopful each of *Saccharomyces cerevisiae* YHK2021 and *Saccharomyces cerevisiae* FSC6012 were respectively inoculated into 5 ml of YPD medium, followed by shaking culture at 28° C. for one day.

Each of the resulting cultures (100 μl) was inoculated into 5 ml of YPA medium (1% (w/v) potassium acetate, 0.5% (w/v) yeast extract and 1% (w/v) peptone, pH 7.0), followed by shaking culture at 28° C. for 4 days to form spores. The resulting culture was centrifuged to collect cells, and the collected cells were washed with sterile water and suspended in 5 ml of a solution of Zymolyase [0.1% (w/v) Zymolyase-20T (Seikagaku Corporation), 0.02% (w/v) 2-mercaptoethanol and 100 mmol/l phosphate buffer (pH 7.0)]. The resulting suspension was incubated at 30° C. for 30 minutes and then at 55° C. for 10 minutes. Thereafter, the cell suspension was diluted with sterile water and spread on YPD plate medium, followed by culturing at 30° C. for 2 days. By the culturing, spore clones of YHK2021 strain and FSC6012 strain were respectively obtained.

One loopful of the spore clones of YHK2021 strain and FSC6012 strain (ratio; ca. 1:1) was inoculated into 5 ml of YPD medium, followed by culturing at 30° C. for one day. The resulting culture was diluted with sterile water and spread on YPD plate medium, followed by culturing at 30° C. for 2 days to obtain a hybrid strain. The hybrid strain was subjected to the above steps (a) to (d) to obtain yeast cells. Then, the volume expansion of dough was measured according to 7 sequent steps of the above steps (i) to (vii), and the amount of generated carbon dioxide gas was measured according to 7 sequent steps of the above steps (i) to (iv) and (viii) to (x). As a result, three strains were obtained which generated, in dough containing 5% sugar, carbon dioxide gas in an amount of not less than 2.0 ml per g of the dough and not less than 1.20 ml per ml of volume expansion of the dough at 38° C. in 60 minutes. One of the three strains was selected and named YHK2766 strain.

EXAMPLE 3

One loopful each of the yeast strains shown in Table 1 [YHK1923 strain, YHK2766 strain, YFR-291 strain and 8 commercial baker's yeast strains (commercial yeasts 1 to 8)] were respectively inoculated on 8 ml of YM slant medium [1 l of water, 10 g of glucose (Kishida Chemical Co., Ltd.), 5 g of peptone (Difco Laboratories Inc.), 3 g of yeast extract (Difco Laboratories Inc.), 3 g of malt extract (Difco Laboratories Inc.) and 20 g of agar (Kishida Chemical Co., Ltd.), pH 6] in a test tube (diameter: 16.5 mm) previously sterilized at 120° C. for 20 minutes, followed by culturing at 30° C. for 2 days.

The commercial baker's yeast strains used above were prepared by suspending each commercial baker's yeast in sterile water, spreading the resulting suspension on YPD plate medium, culturing the yeast at 30° C. for 48 hours to grow colonies, and then separating the strain from the obtained colonies.

One loopful of the yeast obtained by the above culturing was inoculated into YPD medium [30 ml of water, 0.3 g of yeast extract, 0.6 g of polypeptone (Nihon Pharmaceutical Co., Ltd.) and 0.6 g of glucose] in a 300-ml Erlenmeyer flask previously sterilized at 120° C. for 20 minutes, followed by shaking culture at 220 rpm at 30° C. for 24 hours (TB-128RL, Takasaki Scientific Instruments Corp.).

The whole of the obtained culture was inoculated into a molasses medium [300 ml of water, molasses in the amount corresponding to 3% (w/v) sugar, 0.579 g of urea (Kishida Chemical Co., Ltd.), 0.138 g of potassium dihydrogenphosphate (Kishida Chemical Co., Ltd.) and 2 drops of defoaming agent] in a 2-l Erlenmeyer flask with an inclined baffle previously sterilized at 120° C. for 20 minutes, followed by shaking culture at 220 rpm at 30° C. for 24 hours (TB-128RL, Takasaki Scientific Instruments Corp.). The obtained culture was centrifuged at 3,000 rpm at 4° C. for 5 minutes (CR22E, Hitachi Koki Co., Ltd.) to collect cells. The collected cells were washed three times with deionized water, followed by suction filtration using a Nutsche funnel to obtain yeast cells.

Strong flour (100 g, Camellia flour, Nisshin Flour Milling Inc.), a yeast suspension comprising 2 g of the yeast cells obtained above and 20 ml of water, and an aqueous solution comprising 5 g of sugar, 2 g of salt and 42 ml of water were mixed and kneaded using National Complete Mixer at 100 rpm for 2 minutes so that the temperature of the resultant dough became 28 to 30° C. The obtained dough was rounded and packed into a 600-ml glass cylinder [diameter (inner diameter): 5.7 cm, height: 24 cm, thickness: 0.5 cm, with both ends open] which had been previously warmed at 30° C. and whose inside was coated with lubricant oil (Runner, Kyowa Hakko Kogyo Co., Ltd.), from the bottom with the smooth side up. Then, the cylinder was put on a dish previously warmed at 30° C., and after the surface of the dough was flattened with a rolling pin, the upper end of the cylinder was covered with a wet cloth, followed by incubation at 30° C. at 85% relative humidity for 2.5 hours. After the incubation, the dough was taken out and subjected to punching, and two pieces (100 g and 20 g) were divided from the dough.

One of the obtained pieces of dough (100 g) was rounded and packed into the glass cylinder used above from the bottom with the smooth side up. Then, the cylinder was put on the dish used above, and after the surface of the dough was flattened with a rolling pin, the height of the top of the dough was measured and the upper end of the cylinder was covered with a wet cloth, followed by incubation at 38° C. at 85% relative humidity for 60 minutes. After the incubation, the height of the top of the dough was measured again. The volume expansion of the dough was calculated from the difference between the height of the top of the dough before incubation and that after incubation.

The volume expansion of dough can be calculated by the following equation ($\pi$=circular constant).

Volume expansion of dough=[(height of the top of the dough after incubation at 38° C. for 60 minutes)−(height of the top of the dough before incubation)]×(inner diameter of the cylinder/2)$^2$×$\pi$ The other piece of the dough (20 g) was put in a 225-ml sample bottle, and the bottle was capped with a cap having a tube connected to Fermograph II (ATTO Corporation) and kept at 38° C. for 5 minutes. Then, the sample bottle was kept at 38° C. for 60 minutes to measure the amount of carbon dioxide gas generated from the dough by using the Fermograph.

The amount of the yeast cells used above is that employed when the ratio of the dry weight is 33% (w/w). When the ratio of the dry weight was not 33% (w/w), the yeast cells were used in an amount calculated by the following equation in place of that when the ratio of the dry weight is 33% (w/w).

Amount of yeast cells (g)=2×33/ratio of the dry weight to the weight of yeast cells Table 1 below shows the amount of carbon dioxide gas generated per g of dough, the volume expansion per g of dough and the amount of carbon dioxide gas generated per ml of the volume expansion of dough for each of the strains used.

TABLE 1

| Strain | Amount of carbon dioxide gas generated (ml/g of dough) | Volume expansion of dough (ml/g of dough) | Amount of carbon dioxide gas generated per ml of volume expansion (ml) |
|---|---|---|---|
| YHK1923 | 2.67 | 2.15 | 1.24 |
| YHK2766 | 2.94 | 2.15 | 1.37 |
| YFR-291 | 2.60 | 2.20 | 1.18 |
| Com. yeast 1 | 2.64 | 2.40 | 1.10 |
| Com. yeast 2 | 2.51 | 2.25 | 1.12 |
| Com. yeast 3 | 2.60 | 2.25 | 1.16 |
| Com. yeast 4 | 2.57 | 2.40 | 1.07 |
| Com. yeast 5 | 2.41 | 2.25 | 1.07 |
| Com. yeast 6 | 2.51 | 2.25 | 1.12 |
| Com. yeast 7 | 2.65 | 2.25 | 1.18 |
| Com. yeast 8 | 2.54 | 2.35 | 1.08 |

EXAMPLE 4

One loopful each of YHK1923 strain, YFR-291 strain and commercial yeast 2 (Dia Yeast, Kyowa Hakko Kogyo Co., Ltd.) shown in Table 1 were respectively inoculated on 8 ml of YM slant medium in a test tube (diameter: 16.5 mm) previously sterilized at 120° C. for 20 minutes, followed by culturing at 30° C. for 2 days. After the culturing, 5 ml of sterile water was added to the slant medium to suspend cells. The obtained suspension (2.5 ml) was inoculated into a molasses medium (300 ml of water, molasses in the amount corresponding to 3% (w/v) sugar, 0.33 g of potassium dihydrogenphosphate and 0.135 g of urea) in a 2-l Erlenmeyer flask with an inclined baffle previously sterilized at 120° C. for 20 minutes, followed by shaking culture at 220 rpm at 30° C. for 24 hours (TB-128RL, Takasaki Scientific Instruments Corp.).

The whole of the obtained culture was added to a medium (43.2 g of ammonium sulfate, 14 g of potassium dihydrogenphosphate, 2.2 g of magnesium sulfate and 1.8l of water) in a 5-l jar fermenter previously sterilized at 120° C. for 20 minutes, and the resulting mixture was subjected to fed batch culture at 30° C. for 30 hours using 800 ml of a molasses medium (total sugar content: 48% (w/v)) previously sterilized at 120° C. for 5 minutes. During the culturing, the medium was adjusted to pH 5.0 with aqueous ammonia. After the completion of the culturing, the cells were collected from the culture by centrifugation and washed, followed by suction filtration using a Nutsche funnel to obtain yeast cells.

Strong flour (1050 g, Camellia flour, Nisshin Flour Milling Inc.), 30 g of the yeast cells obtained above, 1.5 g of yeast food (PAN DIA C-500, Kyowa Hakko Kogyo Co., Ltd.) and 630 g of water were mixed and kneaded using a bread mixer (SS-151, Kanto Kongoki Kogyo Co., Ltd.) at a low speed for 3 minutes and at a medium low speed for 2 minutes so that the temperature of the resultant dough became 24° C. The obtained dough was fermented at 28° C. for 4 hours. To the fermented dough were added 450 g of strong flour, 75 g of sugar, 30 g of salt, 30 g of skim milk and 390 g of water, and the resulting mixture was kneaded at a low speed for 3 minutes and at a medium low speed for 2 minutes. To the dough was further added 75 g of shortening and the resulting mixture was kneaded at a low speed for 2 minutes, at a medium low speed for 3 minutes and at a medium high speed for 3 minutes so that the temperature of the resultant dough became 27° C.

The obtained dough was allowed to stand at 20 to 25° C. for 20 minutes and a piece of dough (450 g) was divided therefrom. The piece of dough was rounded and allowed to stand at 20 to 25° C. for 20 minutes, followed by punching. Then, the dough was put in a one-loaf bread mold and fermented (proofing) at 38° C. at 85% relative humidity until the top of the dough reached the height of 1.5 cm above the rim of the mold.

The obtained dough was sealed up in a vinyl bag and quickly put in a freezer (−20° C.) for freezing. The amount of the yeast cells used above is that employed when the ratio of the dry weight is 33% (w/w). When the ratio of the dry weight was not 33% (w/w), the yeast cells were used in an amount calculated by the following equation in place of that when the ratio of the dry weight is 33% (w/w).

Amount of yeast cells (g)=30×33/ratio of the dry weight to the weight of yeast cells After one day of freezing, the core of the frozen dough was scraped out in an amount of ca. 1 g and weighed. To the weighed dough was added cold water (4° C.) in an amount (weight) of nine times that of the dough, followed by extraction using a homogenizer (Polytron, KINEMATICA AG, output: 3, one minute) under ice-cooling. The obtained extract was filtered and diluted 10 times to measure the amount of ethanol with a gas chromatograph under the following conditions.

Apparatus:
Gas chromatograph: GC-14B (Shimadzu Corporation)
Column: glass column, outer diameter (5 mm)×inner diameter (2.6 mm)×length (1100 mm) (GL Sciences)
Packing material: Adsorb P-1 (80 to 100 mesh) (Nishio Kogyo Co., Ltd.)
Detector: FID Conditions:
Column oven temperature: 150° C.
Sample-vaporizing room temperature: 190° C.
Detector temperature: 190° C.
Helium flow: 50 ml/minute
Hydrogen pressure: 60 kPa
Air pressure: 50 kPa Table 2 below shows the concentration of ethanol in the dough and the time taken for the top of the dough to reach the height of 1.5 cm above the rim of the mold (proofing time) for each of the strains used.

TABLE 2

| Strain | Concentration of ethanol in dough (% (w/w)/g of dough) | Proofing time (minute) |
| --- | --- | --- |
| YHK1923 | 1.47 | 58 |
| YFR-291 | 1.30 | 52 |
| Commercial yeast 2 | 1.34 | 58 |

EXAMPLE 5

Strong flour (1050 g, Camellia flour, Nisshin Flour Milling Inc.), 30 g of the yeast cells of each strain obtained in Example 4 (YHK1923 strain, YFR-291 strain and commercial yeast 2), 1.5 g of yeast food (PAN DIA C-500, Kyowa Hakko Kogyo Co., Ltd.) and 630 g of water were mixed and kneaded using a bread mixer (SS-151, Kanto Kongoki Kogyo Co., Ltd.) at a low speed for 3 minutes and at a medium low speed for 2 minutes so that the temperature of the resultant dough became 24° C. The obtained dough was fermented at 28° C. for 4 hours. To the fermented dough were added 450 g of strong flour, 75 g of sugar, 30 g of salt, 30 g of skim milk and 390 g of water, and the resulting mixture was kneaded at a low speed for 3 minutes and at a medium low speed for 2 minutes. To the dough was further added 75 g of shortening and the resulting mixture was kneaded at a low speed for 2 minutes, at a medium low speed for 3 minutes and at a medium high speed for 3 minutes so that the temperature of the resultant dough became 27° C. The obtained dough was allowed to stand at 20 to 25° C. for 20 minutes and divided to obtain 4 pieces (220 g each). The pieces of dough were rounded and allowed to stand at 20 to 25° C. for 20 minutes, followed by punching. Then, each dough was put in a two-loaf bread mold (pullman) and fermented at 38° C. at 85% relative humidity until the volume of the dough reached 80% of that of the mold. The obtained dough was baked in an oven (Reel Oven ER-6-401, Fujisawa Seisakusho Co., Ltd.) at 210° C. for 28 minutes to make bread.

The amount of the yeast cells used above is that employed when the ratio of the dry weight is 33% (w/w). When the ratio of the dry weight was not 33% (w/w), the yeast cells were used in an amount calculated by the following equation in place of that when the ratio of the dry weight is 33% (w/w).

Amount of yeast cells (g)=30×33/ratio of the dry weight to the weight of yeast cells The obtained bread was sealed up in a vinyl bag, stored at room temperature for one day, and then cut into slices 1.8 cm thick.

The core of a slice of bread was sampled (ca. 1 g) and the concentration of ethanol in the bread was measured according to the method described in Example 4. The results were as follows: bread obtained using YHK1923 strain, 0.84% (w/w); bread obtained using YFR-291 strain, 0.78% (w/w); and bread obtained using commercial yeast 2, 0.76% (w/w).

Sensory test was carried out on the bread with respect to the flavor by 7 skilled panelists and it was confirmed that all loaves of bread obtained using the above three yeast strains had a good flavor.

The time (days) required for mold sporulation on the bread was measured in the following manner using two slices of bread for each test group. Onto one side of each slice was inoculated a suspension of mold spores prepared by suspending mold spores in a 0.1% (v/v) Tween 80 solution at a density of 5×10² spores/ml. The spore suspension was inoculated onto 25 spots on each slice in an amount of 10 μl per spot. The growth of mold at 25° C. was observed and the time (days) required for sporulation was measured. Observation of mold was carried out twice a day (morning and evening) and the number of spots where sporulation was confirmed was counted.

The suspension of mold spores was prepared in the following manner.

One loopful each of *Penicillium expansum* ATCC-1117, *Rhizopus stolonifer* ATCC-24862 and *Aspergillus niger* ATCC-6275 were respectively inoculated on a slant medium prepared by adding 20 g of malt extract, 20 g of glucose, 1 g of peptone and 20 g of agar to 1 l of water and sterilizing this mixture at 120° C. for 20 minutes, followed by culturing at 25° C. for 7 days. To the slant medium was added 5 ml of a 0.1% (v/v) Tween 80 solution to suspend spores. The resulting suspension was centrifuged to collect the spores, and the collected spores were washed twice with a 0.1% (v/v) Tween 80 solution. To the washed spores was added 5 ml of a 0.1% (v/v) Tween 80 solution to suspend the spores, and the obtained suspension was passed through a 40 μm cell strainer (FALCON) twice. The obtained spore suspension was added to a 15% (v/v) glycerol solution to a density of 5×10⁶ spores/ml and stored in a freeze at −80° C. until the time of use.

The number of spots where sporulation was confirmed at each observation with respect to each of the molds is shown in FIG. 1.

As shown in FIG. 1, all of the molds took a longer time for sporulation on the bread obtained using YHK1923 strain than on those obtained using YFR-291 strain and commercial yeast 2. As the prolongation of time taken for mold sporulation was thus recognized, it was confirmed that the bread obtained using YHK1923 strain had anti-mold effect.

EXAMPLE 6

A hybrid strain of YHK2021 strain and FSC6012 strain was obtained from their spore clones in the same manner as in Example 2, and its yeast cells were obtained according to the above steps (a) to (d). Then, the volume expansion of dough was measured according to 7 sequent steps of the above steps (i) to (vii), and the amount of generated carbon dioxide gas was measured according to 7 sequent steps of the above steps (i) to (iv) and (viii) to (x). As a result, two strains were obtained which generated, in dough containing 5% sugar, carbon dioxide gas in an amount of not less than 2.0 ml per g of the dough and not less than 1.20 ml per ml of volume expansion of the dough at 38° C. in 60 minutes. One of the obtained strains was named YHK2931 strain and was deposited with International Patent Organism Depositary, National Institute of Advanced Industrial Science and Technology, Central 6, 1—1, Higashi 1-chome, Tsukuba-shi, Ibaraki 305-8566, Japan, on May 21, 2002 under the Budapest Treaty with accession No. FERM BP-8046.

EXAMPLE 7

The amount of carbon dioxide gas generated per g of dough, the volume expansion of dough per g of dough and the amount of carbon dioxide gas generated per ml of the volume expansion of dough with the use of YHK2931 strain and commercial yeast 2 were measured in the same manner as in Example 3. The results are shown in Table 3.

TABLE 3

| Strain | Amount of carbon dioxide gas generated (ml/g of dough) | Volume expansion of dough (ml/g of dough) | Amount of carbon dioxide gas generated per ml of volume expansion (ml) |
|---|---|---|---|
| YHK2931 | 3.20 | 2.25 | 1.42 |
| Com. yeast 2 | 2.62 | 2.25 | 1.16 |

EXAMPLE 8

The concentration of ethanol in dough and the proofing time taken for the top of dough to reach the height of 1.5 cm above the rim of the mold with the use of YHK2931 strain and commercial yeast 2 were measured in the same manner as in Example 4. The results are shown in Table 4.

TABLE 4

| Strain | Concentration of ethanol in dough (% (w/w)/g of dough) | Proofing time (minute) |
|---|---|---|
| YHK2931 | 1.88 | 49 |
| Commercial yeast 2 | 1.41 | 58 |

EXAMPLE 9

Loaves of bread were made respectively using YHK2931 strain and commercial yeast 2 in the same manner as in Example 5.

Each bread was sealed up in a vinyl bag, stored at room temperature for one day, and then cut into slices 1.8 cm thick.

The core of a slice of bread was sampled (ca. 1 g) and the concentration of ethanol in the bread was measured according to the method described in Example 4. The concentration of ethanol in the loaves of bread obtained using YHK2931 strain and commercial yeast 2 was 1.0% (w/w) and 0.8% (w/w), respectively.

Sensory test was carried out on the bread with respect to the flavor by 7 skilled panelists and it was confirmed that both loaves of bread obtained using the above two yeast strains had a good flavor.

The time required for mold sporulation on the bread was measured in the same manner as in Example 5. The number of spots where sporulation was confirmed at each observation with respect to each of the molds is shown in FIG. 2.

Figure 2:
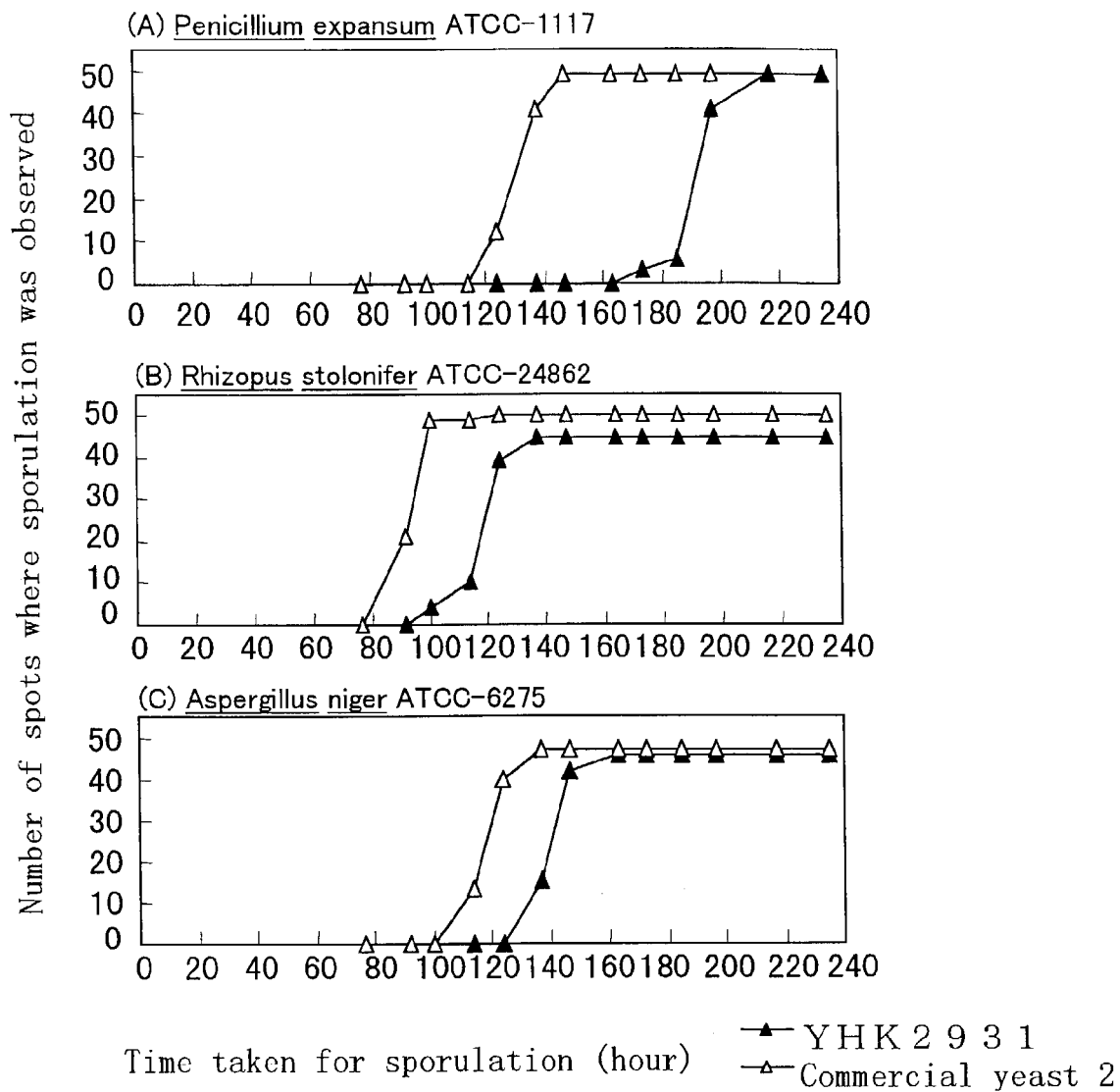
FIG. 2 shows the results of measurement of the time taken for mold to sporulate on two loaves of bread made using YHK2931 strain and commercial yeast 2, respectively. The numbers on the abscissa of each graph indicate the time lapse after the inoculation of mold spores onto bread and those on the ordinate indicate the number of spots where sporulation was observed. The graphs respectively show the results of the measurement of the time taken for mold to sporulate with respect to (A) *Penicillium expansum* ATCC-1117, (B) *Rhizopus stolonifer* ATCC-24862 and (C) *Aspergillus niger* ATCC-6275. The symbols refer to the strains used for production of bread as follows: ▲ YHK2931 strain and Δ commercial yeast 2.

As shown in FIG. 2, all of the molds took a longer time for sporulation on the bread obtained using YHK2931 strain than on that obtained using commercial yeast 2. As the prolongation of time taken for mold sporulation was thus recognized, it was confirmed that the bread obtained using YHK2931 strain had anti-mold effect.

What is claimed is:

1. An isolated yeast belonging to the genus *Saccharomyces*, which generates, in dough containing 5% sugar, carbon dioxide gas in an amount of not less than 2.0 ml per g of the dough and not less than 1.20 ml per ml of volume expansion of the dough at 38° C. in 60 minutes.

2. The isolated yeast according to claim 1, wherein the yeast belongs to *Saccharomyces cerevisiae*.

3. The isolated yeast according to claim 1, wherein the yeast is *Saccharomyces cerevisiae* YHK1923 (FERM BP-7901) or *Saccharomyces cerevisiae* YHK 2931 (FERM BP-8046).

4. Bread dough containing the isolated yeast according to claim 1.

5. A process for making bread which comprises baking the bread dough according to claim 4.

6. Bread obtained by the process according to claim 5.

7. A method of screening for yeast which comprises selecting a yeast belonging to the genus *Saccharomyces* which generates, in dough containing 5% sugar, carbon dioxide gas in an amount of not less than 2.0 ml per g of the dough and not less than 1.20 ml per ml of volume expansion of the dough at 38° C. in 60 minutes.

8. An isolated yeast obtained by the method according to claim 7.

9. Bread dough containing the isolated yeast according to claim 8.

10. A process for making bread which comprises baking the bread dough according to claim 9.

11. Bread obtained by the process according to claim 10.

12. The bread according to claim 11, which has a high ethanol content.

13. The bread according to claim 6, which has a high ethanol content.

14. The isolated yeast according to claim 1, which generates, in said dough, carbon dioxide in an amount of not less than 2.4 ml per g of said dough and not less than 1.40 ml per ml of volume expansion of said dough at 38° C. in 60 minutes.

15. The isolated yeast according to claim 14, which generates in said dough carbon dioxide in an amount of not less than 3.0 ml per g of said dough.

16. The method according to claim 7, wherein, prior to said selecting, a yeast belonging to the genus *Saccharomyces* is subjected to mutagenesis to form mutants, and said mutants are subjected to said selecting.

17. The bread according to claim 6, having an ethanol concentration in a range of 0.8% or higher and below 1.5% (w/w).

18. The bread according to claim 6, having an ethanol concentration of at least 0.8% (w/w).

19. Bread dough containing the isolated yeast according to claim 3.

20. A process for making bread which comprises baking the bread dough according to claim 19.

21. Bread obtained by the process according to claim 20.

* * * * *